(12) United States Patent
Cristobal et al.

(10) Patent No.: US 7,694,814 B1
(45) Date of Patent: Apr. 13, 2010

(54) SEALED MEDICAL DEVICE ENCLOSURE

(75) Inventors: Clifford Cristobal, Redmond, WA (US); Gregory T. Wing, Carnation, WA (US)

(73) Assignee: SonoSite, Inc., Bothell, WA (US)

( * ) Notice: Subject to any disclaimer, the term of this patent is extended or adjusted under 35 U.S.C. 154(b) by 862 days.

(21) Appl. No.: 11/287,463

(22) Filed: Nov. 23, 2005

(51) Int. Cl.
*A61B 17/06* (2006.01)
*A61B 8/14* (2006.01)
*A61B 8/00* (2006.01)

(52) U.S. Cl. ............... 206/438; 600/437; 600/438; 600/459

(58) Field of Classification Search ........... 206/438, 206/363, 560, 565, 570; 220/521, 522, 378
See application file for complete search history.

(56) References Cited

U.S. PATENT DOCUMENTS

| | | | | |
|---|---|---|---|---|
| 4,752,453 A | * | 6/1988 | Nichols | 422/300 |
| 5,098,676 A | * | 3/1992 | Brooks, Jr. | 422/292 |
| 5,281,400 A | * | 1/1994 | Berry, Jr. | 422/295 |
| 5,332,943 A | | 7/1994 | Bhardwaj | |
| 5,372,787 A | * | 12/1994 | Ritter | 422/119 |
| 5,534,221 A | * | 7/1996 | Hillebrenner et al. | 422/33 |
| 5,630,419 A | * | 5/1997 | Ranalletta | 600/459 |
| 5,641,065 A | * | 6/1997 | Owens et al. | 206/370 |
| 5,678,551 A | * | 10/1997 | Stevens | 600/474 |
| 6,117,084 A | * | 9/2000 | Green et al. | 600/459 |
| 6,162,395 A | * | 12/2000 | Kowanko | 422/33 |
| 6,551,298 B1 | * | 4/2003 | Zhang et al. | 604/403 |
| 6,800,987 B2 | | 10/2004 | Toda | |
| 2008/0156805 A1 | * | 7/2008 | Perry et al. | 220/361 |

OTHER PUBLICATIONS

CIVCO Medical Instruments, CIVCO Scanhead Connector Enclosure Box, "Transducer Connector Enclosure Box," p. 1 of 1, Jul. 26, 2005, www.civco.com/products/catalog.

* cited by examiner

*Primary Examiner*—Ehud Gartenberg
*Assistant Examiner*—Jose S Stephens, III
(74) *Attorney, Agent, or Firm*—Fulbright & Jaworski L.L.P.

(57) ABSTRACT

Systems and methods providing an enclosure for protecting portions of a medical device are shown. Embodiments individually protect multiple portions of a medical device during sterilization. Protective enclosures of embodiments provide a minimized size adapted to provide protection to portions of a medical device susceptible to damage by a sterilization process. Enclosures of embodiments provide protection by preventing unauthorized use of the medical device being protected.

7 Claims, 3 Drawing Sheets

SEALED MEDICAL DEVICE ENCLOSURE

TECHNICAL FIELD

The present invention relates generally to sealed enclosures, and more particularly to sealed enclosure for sealing a portion of a medical device.

BACKGROUND OF THE INVENTION

Medical devices used to treat and diagnose patients may come into contact with internal or external areas of the patients, creating a risk of transmitting bacteria, viruses, or other infectious diseases from one patient to another. Sterilization, or the elimination of all transmissible agents (including bacteria, viruses, and other microorganisms), of medical devices, is used to prevent spreading diseases between patients who are treated or diagnosed with the same medical devices.

Methods for sterilizing medical devices are commonly carried out in a device called an autoclave and are performed by using heat, radiation, or chemicals. Heat sterilization exposes a medical device to pressurized steam to sufficiently heat the surfaces of the device to effect sterilization. In order to be effective, the steam needs to impinge all surfaces, thus limiting the size of the item being sterilized by the size of the autoclave. While one of the most widely used methods of sterilization, not all medical devices, or not all parts of a medical device, can survive the requisite temperatures and pressures used in heat sterilization. For example, electrical components and/or particular materials comprising a portion of the medical device may be damaged by the application of such sterilizing steam.

Radiation sterilization exposes all surfaces of a medical device to ionizing radiation, such as gamma radiation, x rays, or high-energy electrons, in order to create charged particles and free radicals within the transmissible agents. The charged particles and free radicals act to damage the inner workings of the agent (such as a bacteria's DNA), thereby killing the agent after enough damage has accumulated. While effective, radiation sterilization requires the use of expensive equipment to handle the source of the ionizing radiation. The size of apparatus for containing and safely delivering such radiation is limited, thus limiting the size of the item being sterilized. Moreover, not all medical devices, or not all parts of a medical device, can survive exposure to such radiation. For example, electrical components and/or particular materials comprising a portion of the medical device may be damaged by the application of such sterilizing radiation.

Chemical sterilization exposes all surfaces of a medical device to chemical compounds, such as ethylene oxide gas or liquid glutaraldehyde, with known sterilizing properties for a fixed amount of time to effect sterilization. While chemical sterilization enables low temperature sterilization without the use of radioactivity, its use is still limited in that the chemical compounds used are toxic and expensive. Not all medical devices, or not all parts of a medical device, can survive exposure to such chemicals. For example, electrical components and/or particular materials comprising a portion of the medical device may be damaged by the application of such sterilizing chemicals.

Ultrasound devices are used by the medical industry to provide images of the muscle and soft tissue of patients. Ultrasound devices may be used in noninvasive procedures, such as during pregnancy to image the developing fetus, or may be used in invasive procedures, such as during surgery to image internal tissue and organs of the patient. Ultrasound devices typically comprise a base unit and a scan head. The base unit is operable to control the scan head, interpret the ultrasonic pulses, and generate the image of the tissue of the patient and typically does not come into contact with any portion of the patient, preventing the need for sterilization. The scan head is generally comprised of an ultrasonic transducer and a cable wherein the cable is sufficiently long to prevent the patient from coming into contact with or otherwise contaminating the base unit. In some configurations, the ultrasound device may provide a connection between the base unit and the ultrasonic transducer, such as to allow the use of differently configured transducers, to allow for their replacement, etc. In operation, the scan head is placed onto or inside of the patient and sends and receives ultrasonic pulses, thus necessitating sterilization.

Generally, a scan head may require sterilization where the base unit may does not. Accordingly, the use of a connector detachably connecting the scan head to the base unit allows the scan head to be separated from and sterilized apart from the base unit, such that the base unit does not need to be designed to withstand sterilization. However, portions of the scan head assembly may not be suitable for exposure the sterilization process. For example, the connector itself may be damaged by the sterilization process. Additionally, the connector of the scan head may contain delicate electrical components that need to be protected from sterilization. However, when used on a patient for imaging, only portions of the of the scan head (the transducer and possibly some portions of the cable) come into contact with the patient. While some portions (the transducer and cable) of the scan head necessitate sterilization, other portions (the connector) need to be protected from sterilization. Protective enclosures that surround the connector are used to protect it from sterilization while still allowing the transducer and cable of the scan head to be sterilized.

The types and sizes of medical devices to be sterilized in an autoclave or other sterilization apparatus are limited by the size of the sterilization apparatus. Yet, a protective enclosure must be large enough to contain, seal, and adequately protect portions of the medical device from sterilization. Prior art protective enclosures for use with scan head assemblies have generally been relatively large, e.g., protecting the entire connector by providing an enclosure fully incarcerating the scan head assembly connector and providing a seal through which the cable to the transducer passes. Such a configuration suffers from disadvantages such as an enclosure which is too large to fit into many sterilization apparatus. Additionally, by closing the seal against the cable, such prior art enclosures may cut into or otherwise damage the cable after repeated sterilizations. Further, as the connector is not held in place within the enclosure, the connector may become damaged by forcefully contacting the enclosure when the scan head is being handled or sterilized.

BRIEF SUMMARY OF THE INVENTION

The present invention is directed to a system and method which provides for an enclosure for protecting portions of a medical device. Embodiments of the invention individually protect multiple portions of a medical device during sterilization. Additionally or alternatively, enclosures of embodiments of the present invention provide protection by preventing unauthorized use of the medical device being protected.

In one embodiment, an enclosure has one seal on each of a plurality of separate sections for sealing against different portions of the medical device to be protected. In one embodiment, the enclosure comprises multiple sections that are hinged together to facilitate the insertion and removal of a portion of a medical device being sterilized and facilitating interfacing the aforementioned seals against appropriate surfaces of the medical device. For example, a connector of an ultrasound scan head assembly may include an electrical component portion in need of protection during sterilization and a locking mechanism, which if not protected during sterilization would result in infiltration of the electrical component portion. The aforementioned seals may operate protect these portions, thereby cooperating to protect the medical device.

Embodiments of the inventions provide a seal disposed to engage a strain relief portion and/or a cable housing portion of a medical device cable assembly, thereby providing a seal through which a cable may pass but which does not engage the cable itself. Such a configuration facilitates accommodating various sizes of cables, using a common strain relief configuration, with a single protective enclosure. Moreover, such a configuration avoids damage to more fragile parts of the cable assembly from repeated use of the protective enclosure.

Embodiments of the invention includes a locking mechanism advantageously adapted to align, secure, and maintain sufficient force to engage the seals against surfaces of the medical device and protect the medical device from sterilization. The foregoing locking mechanism may additionally be used to secure the portion of the medical device inside of the protection enclosure and thus prevent unauthorized use of the medical device. For example, when the protective enclosure provides protection of a scan head connector assembly, the locking mechanism may employ a lock or other keyed release to incarcerate the connector within the protective enclosure and prevent its interfacing with a base unit by unauthorized personnel.

Various configurations of protective enclosures may be implemented according to the present invention. For example, a protective enclosure of the present invention may protect and secure more than one medical device allowing multiple medical devices to be sterilized at the same time. In another embodiment, the enclosure may include portions protected from sterilization, which may further include identifying marks or other components that aid in the use of the enclosure.

It should be appreciated from the above that protective enclosures of embodiments of the present invention provide reduced overall size, thereby facilitating sterilization in various apparatus due to the protective enclosure providing seals to protect select portions of the medical device while leaving other portions unprotected. For example, by sealing against portions of a connector assembly to be protected, components of the connector that may be damaged by the sterilization process are protected whereas other components of the connector that are not susceptible to damage are not protected, although sterilization of these components is unnecessary.

The foregoing has outlined rather broadly the features of the present invention in order that the detailed description of the invention that follows may be better understood. Additional features of the invention will be described hereinafter which forms the subject of the appended claims. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the claims of the invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

The present invention provides for a protective enclosure, that protects portions of a medical device allowing it to be properly sterilized, even though certain portions of the medical device may be susceptible to damage from the sterilization process. Preferred embodiments of the invention provide a protective enclosure which protects multiple portions of a medical device by sealing a plurality of seals against different areas of the medical device, such as different surfaces, each of which is separately sealed.

Figure 1:
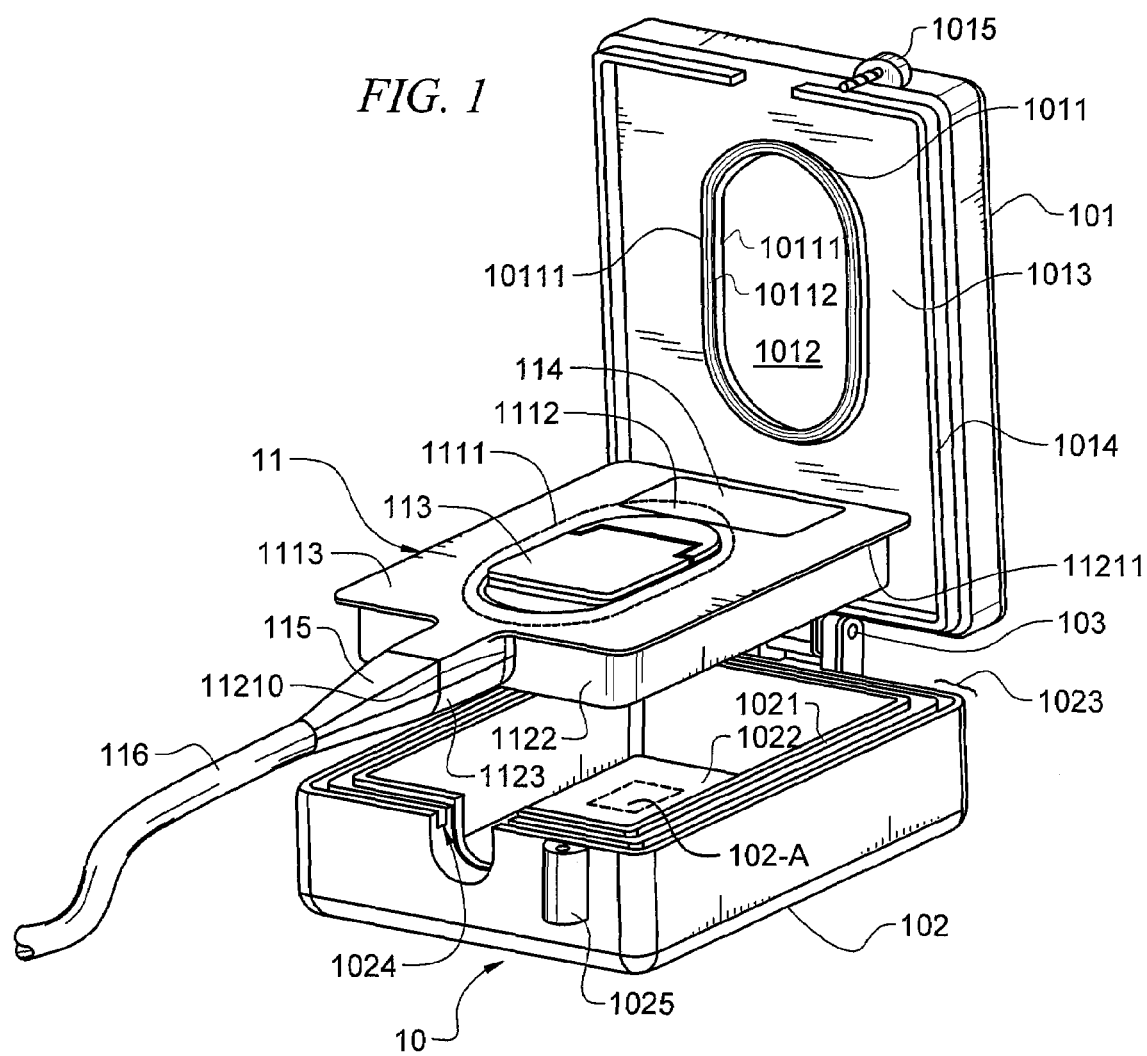
FIG. 1 illustrates one embodiment of a protective enclosure of the present invention in an open position.

Referring to FIG. 1, an embodiment of the invention is shown. In this embodiment, enclosure 10 is comprised of a top section 101 and a bottom section 102, each made from one or more pieces of sufficiently rigid and thermally and/or chemically stable material that can withstand multiple sterilization processes, such as DERLIN or equivalent, anodized aluminum and/or the like. It should be noted that while enclosure 10 is comprised of two sections 101 and 102, any number of sections may be used to make the enclosure according to embodiments of the invention.

Sections 101 and 102 of enclosure 10 are shown, in FIG. 1, in an open position allowing for the insertion of a portion of a medical device to be protected. In this case, the medical device comprises a scan head assembly having an ultrasonic transducer (not shown), cable 116, and connector 11. Connector 11 further comprises cable strain relief 115 and latch 113, which is used to secure the scan head to the base unit of the ultrasonic system. Connector 11 is to be provided protection during the sterilization process. Specifically, an electrical connector portion (not visible on the underside of connector 11) and its attendant electrical components are to be protected. Because latch 113 provides a mechanical mechanism which retains the aforementioned electrical connector in communication with the ultrasound base unit, exposure of latch 113 to the sterilization, or use, may result in infiltration of sterilization gasses or liquids into the electrical connector portion through the body of connector 11. Accordingly, in the illustrated embodiments both the electrical connector portion and latch portion of connector 11 are sealed by enclosure 10. In this embodiment, enclosure 10 has been designed to be as small as reasonably possible and still be operable to protect from sterilization the pertinent portions of the scan head.

Top section 101 and bottom section 102 comprise seals 1011 and 1021, respectively, parts of which are made from a suitable material operable to create an airtight or otherwise appropriate seal between two surfaces when compressed, seals 1011 and 1021 may be made of any suitable resilient material resistant to the effects such as rubber or EPDM (Ethylene Propylene Diene Monomer).

It should be noted that in alternative embodiments of the invention the enclosure may comprise any number of sections, including a single section, and that each section may individually comprise any number of seals, including the case of a section having no seals, so long as the enclosure comprises at least one section and at least one seal. In the case of an enclosure with a single section, one or more seals would be used to properly protect the delicate portions of the medical device. A section with no seals may be used to lend support to the overall structure of the enclosure or as an aid in closing or aligning other sections of the enclosure. Additionally, different medical devices' portions that need protecting may be in different locations, such that an enclosure designed for use with multiple medical devices may, for a given instrument, have seals that protect portions of the instrument that do not need protecting. Further, a single seal may be a part of multiple sections of the enclosure.

Top seal 1011, in this embodiment, is further comprised of ridges 10111 that act to hold and align gasket 10112 in place on top section 101, wherein gasket 10112 forms the seal that protects portions 1012 of top section 101 of enclosure 10 and portion 1112 of connector 11 of the scan head when the enclosure is closed. It should be noted that in having protected portion 1012, the enclosure may comprise delicate components, such as electronics (i.e. sterilization enclosure usage circuitry), that may aid in the use of the enclosure. Such components and their uses may include, but are not limited to, any one or combination of: a timer that may measure the sterilization time; a pressure meter or chemical sensor that may ensure proper functioning of the seals; a locator device that may be used to locate the enclosure; the placement of identifying marks or devices such a bar code or a radio frequency identification (RFID) tag; a counter that may be used for recording the number of times the enclosure has been sterilized; or a general purpose memory device that may be used to store information pertaining to the enclosure, the sterilization history of the enclosure, the medical devices the enclosure may be used with, the medical devices the enclosure has been used with, or the patients who have been diagnosed or treated with the medical devices sterilized with the enclosure.

Top seal 1011 is, in this embodiment, ovally shaped to fit around and protect portion 1112 of connector 11 defined by dotted oval 1111, which includes latch 113, thereby allowing for the protection of latch 113 from sterilization when the enclosure is closed. Bottom seal 1021 is, in this embodiment, shaped to fit around and protect portion 1122 of connector 11 defined by area 1122 that includes the dotted line 11210 on connector portion 1113, 112 and jut 11211. Portion 1122 of connector 11 includes delicate electronics that are protected from damage due to there sterilization process when the enclosure is closed. It should be noted that the seals of the enclosure may take any shape so as to protect at least a portion of a medical device for which the seal of the enclosure is designed.

Top section 101 also includes alignment ridge 1014, which is used in conjunction with alignment slot 1024 on bottom section 102 to properly align sections 101 and 102 when closing enclosure 10 and maintain its alignment during sterilization. It should be noted that various forms of or methods for alignment may be used according to embodiments of the invention to ensure the proper positioning of the sections of the enclosure.

Sections 101 and 102 of enclosure 10 are shown being connected by hinge 103 that operates to: properly align sections 101 and 102, in addition to ridge 1014 and slot 1024; allows for smoothly transitioning between the opening and closing positions of the enclosure; and aids to secure the enclosure when in a closed position. It should be noted that various types or combinations of one or more fasteners may be used to align the sections of the enclosure, to maintain the enclosure in an open or closed position, to maintain the force required to keep the enclosure properly closed, or to secure the enclosure when in a closed position according to embodiments of the invention. Such fasteners may include, but are not limited to: a bracket, a catch, a clamp, a clasp, a clip, a latch, a vice, a hasp, a hinge, a hook, or a snap.

Depression 114 on connector 11 is a part of connector 11 that has been depressed to facilitate the placement of identifying marks for the scan head, connector, or both, which may include, but are not limited to: serial numbers, regulatory approvals, trade names, which type of sterilization enclosures may be used, or which types of sterilization methods may be used. The identifying marks may be made and placed in any conventional manner or combination thereof, including but not limited to: placing a sticker comprising the identifying marks or embossing the material of connector 11 to make the identifying marks. Depression 114 further illustrates that, for the purposes of the invention, a single seal may be pressed against multiple surfaces, textures and features of a medical device while still properly protecting the medical device.

It should be noted that, as described above, latch 113 of connector 11 is a means for attaching and securing the scan head to a base unit of an ultrasound system. As such, in an alternative embodiment of the invention, the enclosure may be advantageously designed to utilize a medical device's attaching means in order to attach, align, or secure the enclosure to the medical device for its protection and security. For example, receiver 102-A may be provided for mating with latch 113 so as to hold connector 11 and at least one section of the enclosure together.

Figure 2:
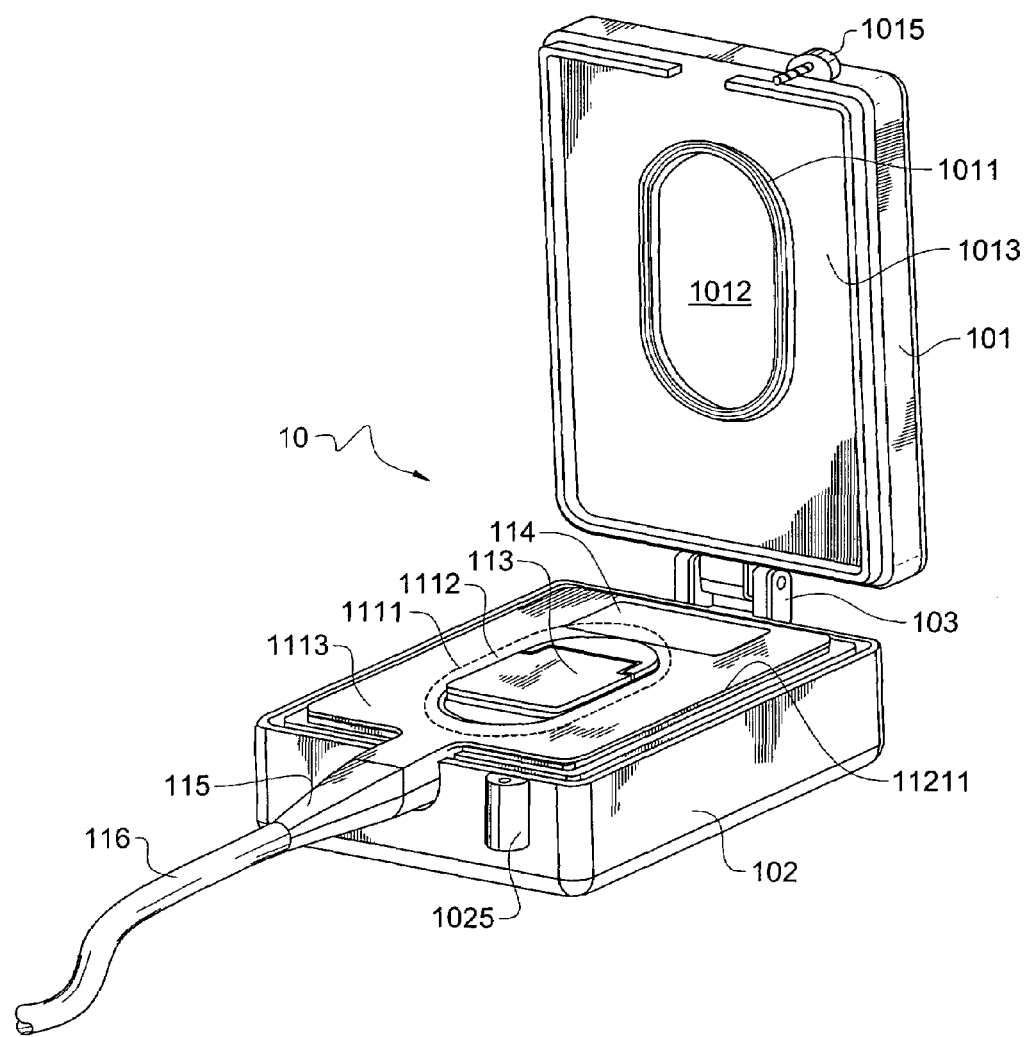
FIG. 2 illustrates the embodiment of the protective enclosure of FIG. 1 having a portion of a medical device to be protected placed inside.

Referring to FIG. 2, connector 11 of the scan head is shown inserted into bottom section 102 of enclosure 10, thereby sealing area 1122 of connector 11, as described above. In the embodiment shown, cable strain relief 115 juts out from bottom section 102 such that enclosure 10 does not seal or press against cable 116, which is further discussed below.

Figure 3:
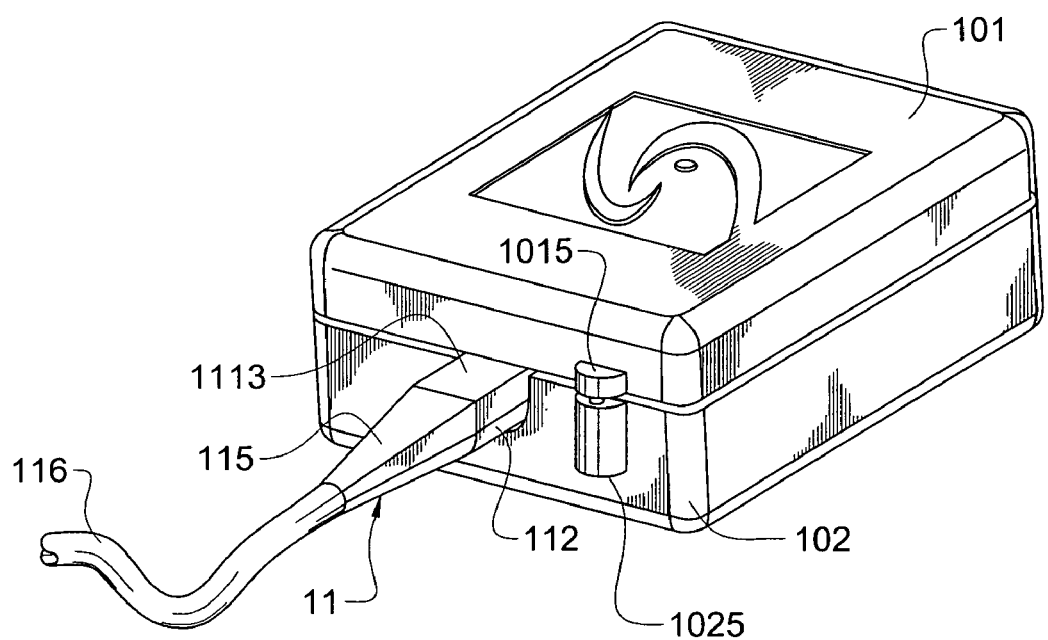
FIG. 3 illustrates the embodiment of the protective enclosure of FIG. 1 in a closed position having a portion of a medical device to be protected placed inside.

Referring to FIG. 3, enclosure 10 is shown in a closed position, containing scan head connector 11, thereby sealing both areas 1122 and 1112 of connector 11. In order to ensure the integrity of the seals and protection of the medical device by the enclosure of the illustrated embodiment, a sufficient force is applied from the enclosure, onto the seals, onto the medical device, protecting the instrument's delicate components. In the embodiment shown in FIGS. 1-3, hinge 103 acts in conjunction with a locking mechanism comprised of lock bolt 1015 and lock hole 1025 to supply sufficient force to the seals of the enclosure. In operation, when sections 101 and 102 have been properly aligned to allow the placement of lock bolt 1015 within lock hole 1025 and a sufficient force has been applied to the enclosure to properly position lock bolt 1015 within lock hole 1025, the locking mechanism engages such that lock bolt 1015 cannot be removed from lock hole 1025 without disengaging the locking mechanism, thereby maintaining a sufficient amount of force upon the seals against the medical device to protect the delicate components. The locking mechanism, when engaged, also secures the medical device from unauthorized use, so long as unauthorized users are unable to disengage the locking mechanism.

As noted above and illustrated in FIGS. 2-3, cable strain relief 115 juts out from bottom section 102 of enclosure 10. Even when enclosure 10 is in a closed position and the locking mechanism has been engaged (FIG. 3), enclosure 10 does not press against any portion of cable 116 and will cause damage to cable 116 due to portions of enclosure 10 straining or pressing against portions of cable 116. It should be noted that alternative embodiments may seal against any portion of the medical device being protected, including the cables of such medical devices.

It should be noted that alternative embodiments may not have a locking mechanism as a part of the enclosure or may implement latching and/or locking mechanisms other than that shown. For example, an embodiment of the invention may utilize a plurality of bail latching mechanisms wherein a bail attached to one section of the enclosure is interfaced with a hook attached to another section with the enclosure. As a bail lever is engaged, the bail may pull the hook, and thus the section of the enclosure, toward the bail mechanism and thus the other section of the enclosure, sealing the enclosure. It should be noted that alternative embodiments may use a different means to maintain force upon the seals of the enclosure, which may or may not include a locking mechanism. Such means include, but are not limited to one or more or a combination of: brackets, catches, clamps, clasps, clips, latches, hasps, hinges, hooks, snaps, or vices.

Alternative embodiments may use different locking mechanisms to secure the medical device from unauthorized use. Such locking mechanisms may utilize, but are not limited to utilizing one or more or a combination of: combinations, keys, tumblers, switches, or magnets. While the locking mechanism of the embodiment of FIGS. 1-3 was advantageously chosen to additionally act as an aligning means and force maintaining means, other locking mechanisms may be used that do not function to align the sections or maintain force against the seals of the enclosure, such as the combination of a hasp integrated to the enclosure and a padlock.

A single protected enclosure of an embodiment of the invention may be adapted so as to allow the insertion of more than one medical device and in doing so, allowing more than one medical device to be sterilized at the same time using a single enclosure. For example, two of connectors 11 may be placed back to back (i.e., having latches 113 thereof facing one another), perhaps with a gasket or other seal disposed there between, and a protective enclosure comprised of two portions configured as bottom section 102 closed thereon to provide a protective enclosure for both such connectors. As another example, an alternative embodiment may be that of a double enclosure comprising two subenclosures similar to that of the embodiment illustrated in FIGS. 1-3 having their respective bottom sections 102 connected side by side, with their respective top sections 101 being either connected or disconnected. Such an arrangement would allow either one of or both subenclosures to be used for protecting one or two connectors 11 during sterilization.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An enclosure comprising:
   at least one body section; and
   a plurality of seals provided in association with said at least one body section, wherein a first seal of said plurality of seals cooperates with said at least one body section to interface with a first portion of a medical device to define a first protective volume, and wherein a second seal of said plurality of seals cooperates with said at least one body section to interface with a second portion of said medical device to define a second protective volume, said first and second protective volumes protecting at least first and second portions of said medical device during sterilization; wherein said first portion comprises a first surface and said second portion comprises a second surface; wherein the first protective volume comprises a volume defined by a surface of said at least one body section, the first surface of the medical device, and the first seal, wherein the first seal forms a boundary of the first protective volume; and wherein the second protective volume comprises a volume defined by a surface of said at least one body section, the second surface of the medical device, and the first seal, wherein the second seal forms a boundary of the first protective volume.

2. The enclosure of claim 1, wherein a circumferential length of said first seal forming said perimeter of the first protective volume is less than a circumferential length of said first surface, and wherein a circumferential length of said second seal forming said boundary of the second protective volume is less than a circumferential length of said second surface.

3. The enclosure of claim 1, wherein said at least one body section comprises a top body section and a bottom body section and is adapted to allow portions of said medical device to extend between the top body section and bottom body section along all points of the peripheries thereof when said first seal interfaces with said first portion of said medical device and said second seal interfaces with said second portion of said medical device.

4. The enclosure of claim 1, wherein said enclosure is adapted to protect a plurality of medical devices from a sterilization process, said plurality of medical devices having different sized signal transmission cables.

5. The enclosure of claim 1, wherein said at least one body section comprises at least two body sections, said at least two body sections each having a seal of said plurality of seals associated therewith.

6. The enclosure of claim 5, further comprising an aligning ridge disposed in a first section of said at least two body sections and a corresponding slot disposed in a second section of said at least two body sections.

7. The enclosure of claim 1, further comprising: sterilization enclosure usage circuitry disposed in at least one of said protective volumes, said sterilization enclosure usage circuitry providing information with respect to usage of said enclosure.

* * * * *